United States Patent [19]

Hauser et al.

[11] Patent Number: 5,143,689

[45] Date of Patent: Sep. 1, 1992

[54] METHOD FOR DETERMINING THE COEFFICIENT OF THERMAL EXPANSION OF COKE

[75] Inventors: Jeffrey B. Hauser, Middleburgh Hts.; Stephen C. Paspek, Broadview Hts.; Harry A. Adams, Bedford Hts., all of Ohio

[73] Assignee: The Standard Oil Company, Cleveland, Ohio

[21] Appl. No.: 821,298

[22] Filed: Jan. 13, 1992

Related U.S. Application Data

[63] Continuation of Ser. No. 612,050, Nov. 9, 1990, abandoned.

[51] Int. Cl.$^5$ ............................................. G01N 25/16
[52] U.S. Cl. ....................................................... 374/55
[58] Field of Search ................... 374/44, 55; 436/145, 436/149; 73/866; 264/29.1, 40.4; 252/502; 423/449

[56] References Cited

U.S. PATENT DOCUMENTS

| | | | |
|---|---|---|---|
| 3,960,704 | 6/1976 | Kegler et al. | 423/445 |
| 4,029,749 | 6/1977 | Murakami | 423/445 |
| 4,071,604 | 2/1978 | Schwemer | 423/449 |
| 4,082,515 | 4/1978 | Capes et al. | 423/445 |
| 4,100,265 | 7/1978 | Yoshimura et al. | 423/445 |
| 4,111,794 | 9/1978 | Pietzka et al. | 423/445 |
| 4,526,834 | 7/1985 | Mercuri et al. | 428/408 |
| 4,631,181 | 12/1986 | Matsumoto et al. | 423/445 |
| 4,636,969 | 2/1987 | Kyoden et al. | 374/55 |
| 4,814,063 | 3/1989 | Murakami et al. | 208/50 |
| 4,822,479 | 4/1989 | Fu et al. | 208/50 |

Primary Examiner—William A. Cuchlinski, Jr.
Assistant Examiner—Diego F. F. Gutierrez
Attorney, Agent, or Firm—Larry W. Evans; David J. Untener; Scott A. McCollister

[57] ABSTRACT

A technique for measuring the coefficient of thermal expansion of calcined petroleum coke. This technique involves pressing a pellet of calcined coke to determine the coefficient of thermal expansion. It has the advantage of eliminating the graphitization and machining steps resulting in reduced manpower and turnaround time and requires less sample which allows CTE determination of laboratory scale cokers. Results show good correlation between this technique and traditional extrusion techniques.

21 Claims, No Drawings

METHOD FOR DETERMINING THE COEFFICIENT OF THERMAL EXPANSION OF COKE

This is a continuation of co-pending application Ser. No. 07/612,050 filed Nov. 9, 1990, now abandoned.

BACKGROUND OF THE INVENTION

This invention relates to a process for determining the coefficient of thermal expansion (CTE) of calcined petroleum coke. The method involves pressing a pellet comprising a mixture of ground petroleum coke and binder pitch, baking the pellet in an inert atmosphere and measuring the expansion of the pellet. This invention results in a fast, low cost determination of coke CTE.

This method is particularly well suited for use in an on-line quality control process. More particularly, this method, because it is rapid and requires only small samples, can be used to quickly monitor the operating conditions in a commercial coker and accordingly maintain optimum coking conditions. Furthermore, the small sample size requirements of this technique permit CTE determinations of research scale coke samples which are too small for standard CTE evaluation techniques.

Needle coke is used in the manufacture of graphite electrodes for the steel industry and is subject to stringent quality criteria regarding its purity and physical properties. A low coefficient of thermal expansion is one of the most critical parameters of coke quality, because it corresponds to the electrodes' thermal shock resistance. Accordingly, it is necessary to know the CTE of coke prior to its use in electrodes. Furthermore, anode coke can be used in the manufacture of electrodes for the aluminum industry. Accordingly, CTE is an important characteristic of anode coke for this use.

The coefficient of thermal expansion is traditionally measured by calcining coke to 1400° C., crushing and mixing the coke with coal tar pitch, extruding a rod, baking it, graphitizing it, machining it, and measuring the CTE by any method known to those skilled in the art. This technique, "extrusion", suffers from three major drawbacks; 1) it requires large samples (at least 1 kg); 2) it is time intensive (at least several days); and 3) it is manpower intensive (many hours of handling).

One method employed for CTE measurement is the "Wilkening Method". Wilkening in the article "Measurement of Thermal Expansion of Petroleum Cokes and Carbon Anodes for Aluminum Production", 19th Biennial Conference on Carbon, State College, PA, June, 1989, pages 472–473, teaches slow melting of coal tar pitch onto a layer of ground coke, baking this to approximately 1000° C. to solidify the mass, cutting a cube from the coke-pitch mixture and measuring the CTE of the cube. This method, however, is manpower intensive because the cube must be machined out of the solidified mixture and has a long preparation time due to an extremely slow baking cycle (5 days).

A method developed by Downing and Borger reduces the time period necessary to determine coke CTE, "A Rapid, Small Scale Method for the Determination of the Thermal Expansion Coefficient of Needle Coke Using Extruded Artifacts" 17th Biennial Conference on Carbon, Lexington, KY, June, 1985, pages 362–363. They show that a mixture of ground coke and coal tar pitch can be extruded into rods and baked for a shorter time period and have good correlation with standard CTE determination methods. More particularly, they showed that the extruded rods can be heated at a much faster rate and a graphitization step can be eliminated by increasing the maximum baking temperature to 1300° C. The net result was that the entire baking cycle would be about 6 hours plus cool down. Although this method shortens the turnaround time necessary for measuring coke CTE, it still involves the time and material intensive extrusion of rods.

SUMMARY OF THE INVENTION

It is a primary objective of this invention to provide a new and improved process for the determination of the CTE of coke.

It is a further objective of this invention to provide a process which determines the CTE of coke in a minimum amount of time.

A still further objective of this invention is to provide a process which can be used to rapidly monitor the CTE of coke produced in a commercial coking operation and optimize the process parameters of the coking operation accordingly.

Another objective of this invention is to provide a CTE determination technique which requires only a small sample size, thus allow CTE determinations from research scale coke samples.

Additional objectives and advantages of the invention will be set forth in part in the description that follows and in part will be obvious from the description or may be learned by the practice of the invention. The objects and advantages of the invention may be realized and attained by means of the instrumentalities and combinations particularly pointed out in the appended claims.

To achieve the foregoing objects and in accordance with the purpose of the invention, as embodied and broadly described herein, the process of this invention comprises grinding a calcined coke sample to a particular mesh size distribution and thoroughly mixing it with a binder pitch in a heated environment. The warm mixture is placed in a heated die and pressed. The formed pellet is removed from the die and baked in a furnace (which has been purged with an inert gas) to carbonize the pellet. Baking consists of exposing the pellet to an increasing furnace temperature up to at least 800° C. After cooling, the pellet is tested in a dilatometer or other analytical device to determine the coke CTE.

DETAILED DESCRIPTION OF THE INVENTION

While the inventive process will be described in connection with a preferred procedure, it will be understood that it is not intended to limit the invention to that procedure. On the contrary it is intended to cover all alternatives, modifications, and equivalents as may be included within the spirit and scope of the invention defined by the appended claims.

In accordance with the invention, the process generally includes repeatedly grinding and sieving a representative sample of calcined coke to a particular size distribution, such as a Tyler −5/+325 mesh size range and preferably a Tyler −20/+50 mesh size range. Preferably, the coke sample weighs less than 100 grams, more preferably the sample comprises about 10 to 20 grams of calcined coke. The coke starting material can be any size calcined coke Tyler 325 mesh or larger, preferably Tyler 200 mesh or larger, however, the exact size distribution is not critical. It is important to note that improved reproducibility is achieved when a sufficient number of large particles are present to properly align and orient in the pressed pellet. A sufficient amount of pitch must also be present to form a relatively high density pellet.

The ground calcined coke is combined with binder pitch in a heated, temperature controlled atmosphere. Preferably, the pitch is coal tar pitch or any petroleum based pitch. The ratio of binder pitch to coke is determined in view of the particular samples coke mesh size distribution and the ultimate pellet size. Generally, the weight ratio of pitch to coke can range from 0.1 to about 1.0. Preferably, the weight ratio of pitch to coke is about 0.25. However, the most preferable ratio of pitch to coke in each mixture must be determined based upon the mesh size distribution of the coke and the characteristics of the particular pitch to allow proper alignment, orientation and density. This can be readily determined by someone of ordinary skill in the art.

The mixing of coke and binder pitch should be performed at a temperature above the softening point of the pitch. Preferably, the mixing temperature is 5° C.-75° C. above the pitch softening point. The mixing must be done at an elevated temperature, otherwise, an unacceptable, low density pellet with structural defects is formed. The mixing can be done by hand with a spatula, with an automated mechanical stirrer, or by any other means known in the art.

It is also important during the hot mixing to protect against overheating of the sample. For example, it has been found that the coal tar pitch when heated to temperatures greater than 160° C. showed significant amounts of undesirable pitch devolatilization (smoking).

After thorough blending, the heated mixture of coke and pitch is placed in a die that has been preheated to at least the softening point temperature of the pitch. Preferably, the die is heated to 5° C.-75° C. above the pitch softening point temperature. The temperature of the die during pressing is maintained above the pitch softening point. The pellet is pressed nominally to at least 1,000 p.s.i. preferably at least 20,000 p.s.i., and most preferably 40,000 p.s.i.

The shape of the die can be particularly significant in the pressing of coke pellets for anisotropic cokes. Cokes such as needle coke are anisotropic (i.e., physical properties measured along one axis are different from those measured along a perpendicular axis). In particular, the CTE value measured along the long axis of the "needles" is much lower than the value measured across the diameter of the needle. Furthermore, anisotropic coke particles tend to align perpendicular to the direction of pressing. To insure reproducible CTE measurements, the degree of alignment must be the same for each pellet.

Micrographs were made of a sectioned cylindrical pellet with a length to diameter ratio much greater than 1 that was pressed along the long axis of the cylinder. The micrographs showed alignment varying along the length of the pellet, with the greatest alignment at the ends of the cylinder in a direction perpendicular to the pressing force vector.

Micrographs of a sectioned parallelpiped pellet, formed with the pressure vector applied to the largest face of the pellet, showed that the coke particles (especially the large coke particles) had fairly uniform alignment perpendicular to the pressing force vector.

Accordingly, the pressing direction, aspect ratio, and particle size distribution are all factors believed to contribute to the reproducibility of the CTE measurement, especially for anisotropic cokes. Therefore, it is desirable to use a die for pressing a pellet which allows uniform and consistent particle orientation. More uniform and consistent orientation can be achieved by pressing against the long face of the pellet. Preferably the die is designed to form a cubic, rectangular or cylindrical pellet, and more preferably a rectangular parallelpiped pellet with the pressure vector being applied perpendicular to the long face.

After pressing, the pellet is removed from the die and baked in an oven or tube furnace (which has been purged with an inert gas such as argon). Proper baking requires that the temperature be increased with time and that the final temperature be sufficient to carbonize the binder pitch. Preferably, the temperature of the furnace is increased to about 1,000° C., and more preferable to about 1,150° C. Sufficient exposure at each progressive temperature must occur to allow the slow devolatilization of the pitch reaction products. Preferably, the temperature is increased from room temperature to peak temperature in about a 12 hour time period (for example, 2.0° C./min.). More preferably, the incremental rate of temperature increase is slowed during the period of time at which the pellet is at those temperatures where the most active devolatilization is occurring (for example, 0.4° C./min.). When coal tar pitch is used, this temperature range is from about 250° C. to about 600° C. These temperature values are dependent on the particular pitch used. This slowed temperature rate increase during the high devolatilization range can extend the length of the baking cycle to 24 hours or more. This type of heating program minimizes puffing of the pellet, loss of density and premature pitch carbonization.

Following baking, the CTE of the pellet is determined by using a dilatometer or other analytical device. Preferably, the measurement is performed along the pellet's long axis. The CTE results determined using the pellet technique correlate well with CTE values calculated by known and accepted extrusion methods. Furthermore, the results are repeatable. A good correlation exists with the standard rod extrusion method over a wide range of CTE values from $0.20 \times 10^{-6}$ per degree centigrade to $1.4 \times 10^{-6}$ per degree centigrade. It is expected that this method can even be used to determine CTE in the range from $-5.0 \times 10^{-6}$ to $20.0 \times 10^{-6}$ °C.$^{-1}$.

Once a correlation to a particular extrusion method is determined, the pellet technique of the present invention can effectively and rapidly determine coke CTE for samples from any feedstock. Of course, the pellet forming and heat treatment techniques are variables which effect the correlation. Accordingly, the coke:-binder ratio, the die shape, pressing force and baking procedure for example must be consistent throughout the establishment of the correlation formulas and subsequent CTE testing.

This method, because of its short cycle time, is particularly applicable to rapidly monitoring a commercial coking operation throughout its cycle, and allows adjustment of coking parameters to yield premium needle coke.

EXAMPLE

A set of 19 pellets were fabricated according to the above method using coke particles of a 0.30–0.85 mm with a coal tar pitch:coke weight ratio of 0.25. The mixture was pressed in a die at a pressure of 40,000 p.s.i. The sample coke was tested with known standard extrusion methods by Union Carbide to determine the CTE. The results are summarized in Table 1.

For these particular experiments a Waage model MP solder pot was used to heat the coal tar pitch/coke mixture. The sieve screens were Tyler 3" standard sieves, 20 and 50 mesh sizes. Pressing was performed using a Carver 50 ton 4 post press. A rectangular parallelpiped pellet die, having nominal dimensions of about 1.5"×0.25"×0.25" was used.

TABLE 1

| Coke Sample | No. of Runs | Green Coke Calcining Temperature, C. | Extrusion CTE Value, $\times 10^{-6}/C$ | Average Pellet CTE Value, $\times 10^{-6}/C$ |
|---|---|---|---|---|
| A | 1 | 1,400 | 0.80 | 3.08 |
| B | 1 | 1,400 | 0.96 | 3.33 |
| C | 1 | 1,400 | 1.43 | 3.98 |
| D | 1 | 1,400 | 1.25 | 3.35 |
| E | 5 | 1,400 | 0.20 | 1.82 |
| F | 5 | 1,400 | 0.30 | 2.03 |
| G | 5 | 1,400 | 0.40 | 2.39 |

CTE values were obtained for each sample using the method of the present invention and then compared to the known CTE value for each sample as determined by a particular extrusion technique. The comparison, by a least squares analysis, showed good correlation between the testing methods according to the two formulas:

For Pellet $CTE > 2.39° C.^{-1}$ $$\text{Extrusion } CTE = (0.653 \times \text{pellet } CTE) - 1.134° C.^{-1} \quad \text{Formula 1.}$$

For Pellet $CTE \leq 2.39° C.^{-1}$ $$\text{Extrusion } CTE = [(0.135 \times \text{pellet } CTE) - 0.236]^{0.5} + 0.103° C.^{-1} \quad \text{Formula 2.}$$

For example, the pellet CTE value of sample A is determined to be $3.08 ° C.^{-1}$. This value when used as the "pellet CTE" variable in formula 1, suggests the extrusion CTE value would be $0.88 ° C.^{-1}$. This is a good correlation with the extrusion determined CTE value of $0.80 ° C.^{-1}$. Sample E was found to have a pellet CTE value of $1.82 ° C.^{-1}$, when this was used with formula 2, the predicted extrusion CTE value is $0.20 ° C.^{-1}$. The CTE value determined by the extrusion method was also $0.20 ° C.^{-1}$.

As described above, the pellet technique is appropriate for rapidly determining an absolute CTE value by correlating the pellet value to the CTE established by using a known extrusion technique. It is also understood, that the pellet technique can effectively be used to compare CTE values from different cokes and establish the relative quality of each coke. Accordingly, it is not necessary to know the established CTE of a coke to rapidly compare coke from different processes. This would allow the rapid monitoring of a coking operation.

Thus, it is apparent that there has been provided in accordance with the invention a process that fully satisfies the objects, aims, and advantages set forth above. While the invention has been described in conjunction with specific embodiments thereof, it is evident that many alternatives, modifications and variations will be apparent to those skilled in the art in light of the foregoing description. Accordingly, it is intended to embrace all such alternatives, modifications, and variations as fall within the spirit and broad scope of the appended claims.

What is claimed is:

1. A method for determining the coefficient of thermal expansion of coke, comprising:
   (a) grinding a coke sample;
   (b) mixing said coke sample with a binder pitch in a heated environment;
   (c) hot pressing to at least 1000 p.s.i. the heated mixture of said coke and said binder pitch in a die to form a pellet;
   (d) baking said pellet to at least 800° C.;
   (e) measuring the thermal expansion of said pellet; and
   (f) calculating the thermal expansion of said coke from the thermal expansion of said pellet.

2. The method of claim 1, wherein the ratio of said pitch to said coke sample is from 0.1 to 1.0.

3. The method of claim 2, wherein the ratio of said pitch to said coke sample is about 0.25.

4. The method of claim 1, wherein said coke sample is ground to a mesh size distribution of about Tyler $-20/+50$.

5. The method of claim 1, wherein said coke sample weighs less than 100 grams.

6. The method of claim 1, wherein said coke sample before grinding is greater than a 50 mesh size distribution.

7. The method of claim 5, wherein said coke sample weighs about 5 grams.

8. The method of claim 7, wherein said pitch comprises about 1.25 grams.

9. The method of claim 1, wherein said mixing occurs at a temperature above a softening point of said binder pitch.

10. The method of claim 9, wherein said mixing occurs at a temperature about 5° C. to 75° C. above the softening point of said pitch.

11. The method of claim 1, wherein said pressing occurs at a temperature above the softening point of said binder pitch.

12. The method of claim 11, wherein said pressing occurs at a temperature about 5° C. to 75° C. above the softening point of said pitch.

13. The method of claim 1, wherein said baking begins at room temperature and is increased to a temperature sufficient to carbonize said binder pitch.

14. The method of claim 13, wherein said pellet is baked to about 1,150° C.

15. The method of claim 13, wherein the rate of increase in baking temperature is slowed during said pellets most active devolatilization period.

16. The method of claim 15, wherein said most active devolatilization period occurs at from about 250° C. to about 600° C.

17. The method of claim 1, wherein said pressing is perpendicular to the longest face of said pellet.

18. The method of claim 17, wherein said die is rectangular parallellpiped shaped.

19. The method of claim 1, wherein said hot pressing occurs at greater than 10,000 p.s.i.

20. The method of claim 1, wherein the thermal expansion of said pellet is correlated to the known coefficient of thermal expansion of said coke sample to determine an absolute coefficient of thermal expansion.

21. A method for determining the thermal expansion of a coke pellet, comprising:
 (a) grinding a coke sample;
 (b) mixing said coke sample with a binder pitch in a heated environment;
 (c) hot pressing to at least 1000 p.s.i. the heated mixture of said coke and said binder pitch in a die to form a pellet;
 (d) baking said pellet to at least 800° C., wherein the rate of increase in baking temperature is slowed during said pellet's most active devolatilization period; and
 (e) measuring the thermal expansion of said pellet.

* * * * *